(12) United States Patent
Zhang et al.

(10) Patent No.: US 11,363,815 B2
(45) Date of Patent: Jun. 21, 2022

(54) TRIFLUOROETHYL THIOETHER (SULFOXIDE) SUBSTITUTED BENZENE COMPOUND AND USE THEREOF

(71) Applicant: SHENYANG UNIVERSITY OF CHEMICAL TECHNOLOGY, Shenyang (CN)

(72) Inventors: Lixin Zhang, Shenyang (CN); Jing Zhang, Shenyang (CN); Po Zhang, Shenyang (CN); Zhuo Kang, Shenyang (CN)

(73) Assignee: SHENYANG UNIVERSITY OF CHEMICAL TECHNOLOGY, Shenyang (CN)

( * ) Notice: Subject to any disclaimer, the term of this patent is extended or adjusted under 35 U.S.C. 154(b) by 0 days.

(21) Appl. No.: 16/972,042

(22) PCT Filed: May 29, 2019

(86) PCT No.: PCT/CN2019/088913
§ 371 (c)(1),
(2) Date: Dec. 4, 2020

(87) PCT Pub. No.: WO2019/233321
PCT Pub. Date: Dec. 12, 2019

(65) Prior Publication Data
US 2021/0244026 A1 Aug. 12, 2021

(30) Foreign Application Priority Data

Jun. 5, 2018 (CN) .......................... 201810569145.1

(51) Int. Cl.
*C07C 323/42* (2006.01)
*C07D 209/46* (2006.01)
*A01N 43/38* (2006.01)

(52) U.S. Cl.
CPC ............ *A01N 43/38* (2013.01); *C07C 323/42* (2013.01); *C07D 209/46* (2013.01)

(58) Field of Classification Search
CPC .......................... C07D 209/46; C07C 323/42
See application file for complete search history.

(56) References Cited

U.S. PATENT DOCUMENTS

| 2012/0053052 A1 | 3/2012 | Gross et al. |
| 2016/0194285 A1 | 7/2016 | Thompson et al. |

FOREIGN PATENT DOCUMENTS

| CN | 101139308 A | 3/2008 |
| CN | 102341376 A | 2/2012 |
| CN | 104995193 A | 10/2015 |
| CN | 105153013 A | 12/2015 |
| CN | 105601577 A | 5/2016 |
| CN | 105722830 A | 6/2016 |
| CN | 207813852 U | 9/2018 |
| EP | 2403837 A1 | 1/2012 |
| JP | 2008308448 A | 12/2008 |
| JP | 2011042611 A | 3/2011 |
| JP | 2012519662 A | 8/2012 |
| WO | 9916743 A1 | 4/1999 |
| WO | 2001042182 A2 | 6/2001 |
| WO | 2001042183 A2 | 6/2001 |
| WO | 2001042185 A2 | 6/2001 |
| WO | 2002060886 A1 | 8/2002 |
| WO | 2004011450 A1 | 2/2004 |
| WO | 2007131680 A1 | 11/2007 |
| WO | 2008023810 A1 | 2/2008 |
| WO | 2010100189 A1 | 9/2010 |
| WO | 2013030262 A1 | 3/2013 |
| WO | 2013030319 A2 | 3/2013 |
| WO | 2013030338 A2 | 3/2013 |
| WO | 2013092350 A1 | 6/2013 |
| WO | 2013157229 A1 | 10/2013 |
| WO | 2014014835 A2 | 1/2014 |
| WO | 2014202505 A1 | 12/2014 |
| WO | 2014202510 A1 | 12/2014 |
| WO | 2015004028 A1 | 1/2015 |

(Continued)

OTHER PUBLICATIONS

Bunce et al.; "Steric and Electronic Requirements in the Synthesis of 2,3-Dihydro-4(1H)-quinolinones by the Tandem Michael-SNAr Reaction"; Journal of Heterocyclic Chemistry; 52(4), pp. 1143-1149 (2015).

(Continued)

*Primary Examiner* — Shawquia Jackson
(74) *Attorney, Agent, or Firm* — Hauptman Ham, LLP

(57) ABSTRACT

The present invention belongs to the field of agricultural acaricides, and particularly relates to a trifluoroethyl thioether (sulfoxide) substituted benzene compound and use thereof. The compound has a structure as shown in general formula I:

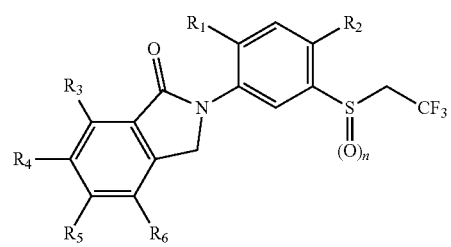

The definition of each substituent in the formula is described in the specification. The compound of general formula I has excellent acaricidal activity and can be used to prevent and control various pest mites.

7 Claims, No Drawings

(56) References Cited

FOREIGN PATENT DOCUMENTS

| | | |
|---|---|---|
| WO | 2015036377 A1 | 3/2015 |
| WO | 2018015852 A1 | 1/2018 |
| WO | 2018051252 A2 | 3/2018 |

OTHER PUBLICATIONS

International Search Report in PCT/CN2019/088913; dated Sep. 3, 2019; 5 pgs.

TRIFLUOROETHYL THIOETHER (SULFOXIDE) SUBSTITUTED BENZENE COMPOUND AND USE THEREOF

RELATED APPLICATIONS

The present application is a National Phase of International Application Number PCT/CN2019/088913, filed May 29, 2019, and claims priority to Chinese Application Number 201810569145.1, filed Jun. 5, 2018.

TECHNICAL FIELD

The present invention belongs to the field of agricultural acaricides, and particularly relates to a trifluoroethyl thioether (sulfoxide) substituted benzene compound and use thereof.

BACKGROUND

In recent years, due to the long term use of existing acaricides, the pest mites have been induced to generate serious resistance, leading to extreme difficulty in prevention and control thereof. Therefore, it is necessary to continuously develop more efficient acaricides with unique mechanism of action.

Patent CN102341376A discloses a compound with certain acaricidal activity as shown in a general formula below.

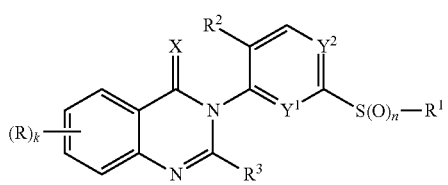

CN102341376A

In the prior art, the compound shown in the general formula I of the present invention and the acaricidal activity thereof haven't been reported yet.

SUMMARY OF THE INVENTION

The purpose of the present invention is to provide a trifluoroethyl thioether (sulfoxide) substituted benzene compound which can control a variety of pest mites at a very small dose, and can be applied to prevent and control of pest mites in the fields of agriculture, forestry and health.

The technical solution of the present invention is as follows.

A trifluoroethyl thioether (sulfoxide) substituted benzene compound is shown in the general formula I:

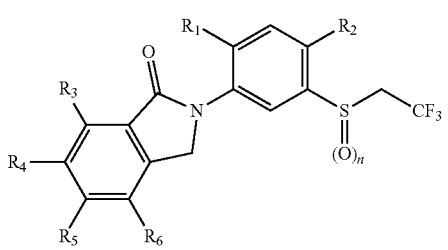

I where:
$R_1$, $R_2$ are independently selected from hydrogen, halogen, cyano, $C_1$-$C_4$ alkyl or $C_1$-$C_4$ haloalkyl; n is selected from 0 or 1;
$R_3$, $R_4$, $R_5$ and $R_6$ are independently selected from hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy.

A preferred compound in the present invention is shown in the general formula I, where:
$R_1$, $R_2$ are independently selected from hydrogen, fluorine, chlorine, bromine, cyano or methyl;
n is selected from 0 or 1;
$R_3$, $R_4$, $R_5$ and $R_6$ are independently selected from hydrogen, fluorine, chlorine, bromine, cyano, nitro, methyl, ethyl, n-propyl, isopropyl, n-butyl, isobutyl, tert-butyl, trifluoromethyl, methoxy, ethoxy or trifluoromethoxy.

A further preferred compound in the present invention is shown in the general formula I, where:
$R_1$ is selected from fluorine;
$R_2$ is selected from methyl;
n is selected from 0 or 1;
$R_3$, $R_4$ and $R_6$ are selected from hydrogen;
$R_5$ is selected from hydrogen or cyano.

The present invention also includes an intermediate compound as shown in the general formula II, which can be used for preparing the compound of the general formula I:

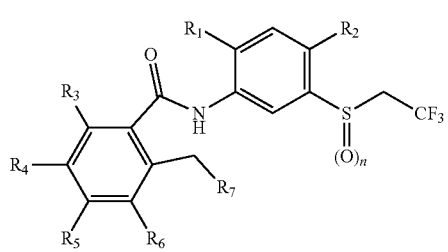

II where:
$R_1$, $R_2$ are independently selected from hydrogen, halogen, cyano, $C_1$-$C_4$ alkyl or $C_1$-$C_4$ haloalkyl; n is selected from 0 or 1;
$R_1$, $R_4$, $R_5$ and $R_6$ are independently selected from hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy;
$R_7$ is selected from chlorine or bromine.

A preferred compound in the present invention is shown in the general formula II, where:
$R_1$, $R_2$ are independently selected from hydrogen, fluorine, chlorine, bromine, cyano or methyl; n is selected from 0 or 1;
$R_3$, $R_4$, $R_5$ and $R_6$ are independently selected from hydrogen, fluorine, chlorine, bromine, cyano, nitro, methyl, ethyl, n-propyl, isopropyl, n-butyl, isobutyl, tert-butyl, trifluoromethyl, methoxy, ethoxy or trifluoromethoxy;
$R_7$ is selected from chlorine or bromine.

A further preferred compound in the present invention is shown in the general formula I, where:
$R_1$ is selected from fluorine;
$R_2$ is selected from methyl;
n is selected from 0 or 1;
$R_3$, $R_4$ and $R_6$ are selected from hydrogen;
$R_5$ is selected from hydrogen or cyano;
$R_7$ is selected from chlorine.

In the above definition of the compound of the general formula I, halogen refers to fluorine, chlorine, bromine or iodine; alkyl refers to linear or branched alkyl, such as methyl, ethyl, n-propyl, isopropyl or different butyl isomers; haloalkyl refers to linear or branched alkyl, on which hydrogen atoms can be partially or completely substituted by halogen, such as chloromethyl, dichloromethyl, trichloromethyl, fluoromethyl, difluoromethyl, trifluoromethyl, 2,2,2-trifluoroethyl, etc.; alkoxy refers to linear or branched alkyl, which is bonded to the structure through an oxygen atom, such as methoxy, ethoxy, tert-butoxy, etc.; haloalkoxy refers to alkoxy on which hydrogen atoms can be partially or completely substituted by halogen, such as chloromethoxy, dichloromethoxy, trichloromethoxy, fluoromethoxy, difluoromethoxy, trifluoromethoxy, chlorofluoromethoxy, trifluoroethoxy, etc.

Some compounds of the general formula I of the present invention are shown in Table 1 and some compounds of the general formula II are shown in Table 2, but the present invention is by no means limited to these compounds.

TABLE 1

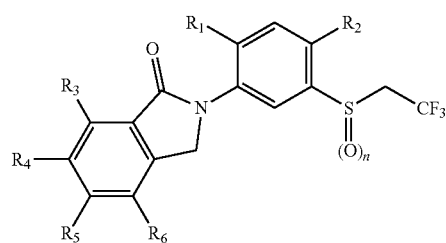

I

| No. | $R_1$ | $R_2$ | $R_3$ | $R_4$ | $R_5$ | $R_6$ | n |
|---|---|---|---|---|---|---|---|
| 1 | F | Me | H | H | H | H | 0 |
| 2 | F | Me | H | H | H | H | 1 |
| 3 | Cl | Me | H | H | H | H | 0 |
| 4 | Cl | Me | H | H | H | H | 1 |
| 5 | Br | Me | H | H | H | H | 0 |
| 6 | Br | Me | H | H | H | H | 1 |
| 7 | Me | Me | H | H | H | H | 0 |
| 8 | Me | Me | H | H | H | H | 1 |
| 9 | CN | Me | H | H | H | H | 0 |
| 10 | CN | Me | H | H | H | H | 1 |
| 11 | F | F | H | H | H | H | 0 |
| 12 | F | F | H | H | H | H | 1 |
| 13 | F | Cl | H | H | H | H | 0 |
| 14 | F | Cl | H | H | H | H | 1 |
| 15 | F | CN | H | H | H | H | 0 |
| 16 | F | CN | H | H | H | H | 1 |
| 17 | Cl | CN | H | H | H | H | 0 |
| 18 | Cl | CN | H | H | H | H | 1 |
| 19 | Br | CN | H | H | H | H | 0 |
| 20 | Br | CN | H | H | H | H | 1 |
| 21 | Cl | Cl | H | H | H | H | 0 |
| 22 | Cl | Cl | H | H | H | H | 1 |
| 23 | Br | Br | H | H | H | H | 0 |
| 24 | Br | Br | H | H | H | H | 1 |
| 25 | F | Me | H | F | H | H | 0 |
| 26 | F | Me | H | F | H | H | 1 |
| 27 | Cl | Me | H | F | H | H | 0 |
| 28 | Cl | Me | H | F | H | H | 1 |
| 29 | Br | Me | H | F | H | H | 0 |
| 30 | Br | Me | H | F | H | H | 1 |
| 31 | Me | Me | H | F | H | H | 0 |
| 32 | Me | Me | H | F | H | H | 1 |
| 33 | CN | Me | H | F | H | H | 0 |
| 34 | CN | Me | H | F | H | H | 1 |
| 35 | F | F | H | F | H | H | 0 |
| 36 | F | F | H | F | H | H | 1 |
| 37 | F | Cl | H | F | H | H | 0 |
| 38 | F | Cl | H | F | H | H | 1 |
| 39 | F | CN | H | F | H | H | 0 |

TABLE 1-continued

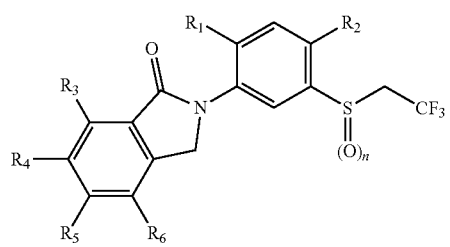

I

| No. | $R_1$ | $R_2$ | $R_3$ | $R_4$ | $R_5$ | $R_6$ | n |
|---|---|---|---|---|---|---|---|
| 40 | F | CN | H | F | H | H | 1 |
| 41 | Cl | CN | H | F | H | H | 0 |
| 42 | Cl | CN | H | F | H | H | 1 |
| 43 | Br | CN | H | F | H | H | 0 |
| 44 | Br | CN | H | F | H | H | 1 |
| 45 | Cl | Cl | H | F | H | H | 0 |
| 46 | Cl | Cl | H | F | H | H | 1 |
| 47 | Br | Br | H | F | H | H | 0 |
| 48 | Br | Br | H | F | H | H | 1 |
| 49 | F | Me | H | H | F | H | 0 |
| 50 | F | Me | H | H | F | H | 1 |
| 51 | Cl | Me | H | H | F | H | 0 |
| 52 | Cl | Me | H | H | F | H | 1 |
| 53 | Br | Me | H | H | F | H | 0 |
| 54 | Br | Me | H | H | F | H | 1 |
| 55 | Me | Me | H | H | F | H | 0 |
| 56 | Me | Me | H | H | F | H | 1 |
| 57 | CN | Me | H | H | F | H | 0 |
| 58 | CN | Me | H | H | F | H | 1 |
| 59 | F | F | H | H | F | H | 0 |
| 60 | F | F | H | H | F | H | 1 |
| 61 | F | Cl | H | H | F | H | 0 |
| 62 | F | Cl | H | H | F | H | 1 |
| 63 | F | CN | H | H | F | H | 0 |
| 64 | F | CN | H | H | F | H | 1 |
| 65 | Cl | CN | H | H | F | H | 0 |
| 66 | Cl | CN | H | H | F | H | 1 |
| 67 | Br | CN | H | H | F | H | 0 |
| 68 | Br | CN | H | H | F | H | 1 |
| 69 | Cl | Cl | H | H | F | H | 0 |
| 70 | Cl | Cl | H | H | F | H | 1 |
| 71 | Br | Br | H | H | F | H | 0 |
| 72 | Br | Br | H | H | F | H | 1 |
| 73 | F | Me | H | CN | H | H | 0 |
| 74 | F | Me | H | CN | H | H | 1 |
| 75 | Cl | Me | H | CN | H | H | 0 |
| 76 | Cl | Me | H | CN | H | H | 1 |
| 77 | Br | Me | H | CN | H | H | 0 |
| 78 | Br | Me | H | CN | H | H | 1 |
| 79 | Me | Me | H | CN | H | H | 0 |
| 80 | Me | Me | H | CN | H | H | 1 |
| 81 | CN | Me | H | CN | H | H | 0 |
| 82 | CN | Me | H | CN | H | H | 1 |
| 83 | F | F | H | CN | H | H | 0 |
| 84 | F | F | H | CN | H | H | 1 |
| 85 | F | Cl | H | CN | H | H | 0 |
| 86 | F | Cl | H | CN | H | H | 1 |
| 87 | F | CN | H | CN | H | H | 0 |
| 88 | F | CN | H | CN | H | H | 1 |
| 89 | Cl | CN | H | CN | H | H | 0 |
| 90 | Cl | CN | H | CN | H | H | 1 |
| 91 | Br | CN | H | CN | H | H | 0 |
| 92 | Br | CN | H | CN | H | H | 1 |
| 93 | Cl | Cl | H | CN | H | H | 0 |
| 94 | Cl | Cl | H | CN | H | H | 1 |
| 95 | Br | Br | H | CN | H | H | 0 |
| 96 | Br | Br | H | CN | H | H | 1 |
| 97 | F | Me | H | H | CN | H | 0 |
| 98 | F | Me | H | H | CN | H | 1 |
| 99 | Cl | Me | H | H | CN | H | 0 |
| 100 | Cl | Me | H | H | CN | H | 1 |
| 101 | Br | Me | H | H | CN | H | 0 |
| 102 | Br | Me | H | H | CN | H | 1 |
| 103 | Me | Me | H | H | CN | H | 0 |
| 104 | Me | Me | H | H | CN | H | 1 |

TABLE 1-continued

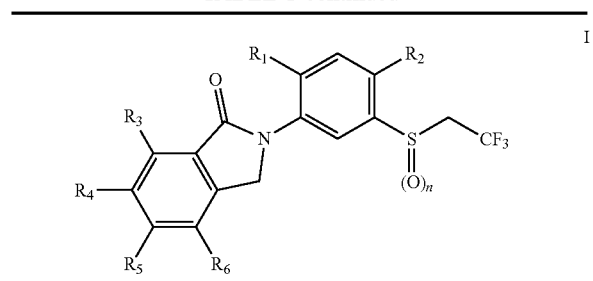

| No. | $R_1$ | $R_2$ | $R_3$ | $R_4$ | $R_5$ | $R_6$ | n |
|---|---|---|---|---|---|---|---|
| 105 | CN | Me | H | H | CN | H | 0 |
| 106 | CN | Me | H | H | CN | H | 1 |
| 107 | F | F | H | H | CN | H | 0 |
| 108 | F | F | H | H | CN | H | 1 |
| 109 | F | Cl | H | H | CN | H | 0 |
| 110 | F | Cl | H | H | CN | H | 1 |
| 111 | F | CN | H | H | CN | H | 0 |
| 112 | F | CN | H | H | CN | H | 1 |
| 113 | Cl | CN | H | H | CN | H | 0 |
| 114 | Cl | CN | H | H | CN | H | 1 |
| 115 | Br | CN | H | H | CN | H | 0 |
| 116 | Br | CN | H | H | CN | H | 1 |
| 117 | Cl | Cl | H | H | CN | H | 0 |
| 118 | Cl | Cl | H | H | CN | H | 1 |
| 119 | Br | Br | H | H | CN | H | 0 |
| 120 | Br | Br | H | H | CN | H | 1 |
| 121 | F | Me | H | Cl | H | H | 0 |
| 122 | F | Me | H | Cl | H | H | 1 |
| 123 | Cl | Me | H | Cl | H | H | 0 |
| 124 | Cl | Me | H | Cl | H | H | 1 |
| 125 | Br | Me | H | Cl | H | H | 0 |
| 126 | Br | Me | H | Cl | H | H | 1 |
| 127 | Me | Me | H | Cl | H | H | 0 |
| 128 | Me | Me | H | Cl | H | H | 1 |
| 129 | CN | Me | H | Cl | H | H | 0 |
| 130 | CN | Me | H | Cl | H | H | 1 |
| 131 | F | F | H | Cl | H | H | 0 |
| 132 | F | F | H | Cl | H | H | 1 |
| 133 | F | Cl | H | Cl | H | H | 0 |
| 134 | F | Cl | H | Cl | H | H | 1 |
| 135 | F | CN | H | Cl | H | H | 0 |
| 136 | F | CN | H | Cl | H | H | 1 |
| 137 | Cl | CN | H | Cl | H | H | 0 |
| 138 | Cl | CN | H | Cl | H | H | 1 |
| 139 | Br | CN | H | Cl | H | H | 0 |
| 140 | Br | CN | H | Cl | H | H | 1 |
| 141 | Cl | Cl | H | Cl | H | H | 0 |
| 142 | Cl | Cl | H | Cl | H | H | 1 |
| 143 | Br | Br | H | Cl | H | H | 0 |
| 144 | Br | Br | H | Cl | H | H | 1 |
| 145 | F | Me | H | H | Cl | H | 0 |
| 146 | F | Me | H | H | Cl | H | 1 |
| 147 | Cl | Me | H | H | Cl | H | 0 |
| 148 | Cl | Me | H | H | Cl | H | 1 |
| 149 | Br | Me | H | H | Cl | H | 0 |
| 150 | Br | Me | H | H | Cl | H | 1 |
| 151 | Me | Me | H | H | Cl | H | 0 |
| 152 | Me | Me | H | H | Cl | H | 1 |
| 153 | CN | Me | H | H | Cl | H | 0 |
| 154 | CN | Me | H | H | Cl | H | 1 |
| 155 | F | F | H | H | Cl | H | 0 |
| 156 | F | F | H | H | Cl | H | 1 |
| 157 | F | Cl | H | H | Cl | H | 0 |
| 158 | F | Cl | H | H | Cl | H | 1 |
| 159 | F | CN | H | H | Cl | H | 0 |
| 160 | F | CN | H | H | Cl | H | 1 |
| 161 | Cl | CN | H | H | Cl | H | 0 |
| 162 | Cl | CN | H | H | Cl | H | 1 |
| 163 | Br | CN | H | H | Cl | H | 0 |
| 164 | Br | CN | H | H | Cl | H | 1 |
| 165 | Cl | Cl | H | H | Cl | H | 0 |
| 166 | Cl | Cl | H | H | Cl | H | 1 |
| 167 | Br | Br | H | H | Cl | H | 0 |
| 168 | Br | Br | H | H | Cl | H | 1 |
| 169 | F | Me | H | Br | H | H | 0 |

TABLE 1-continued

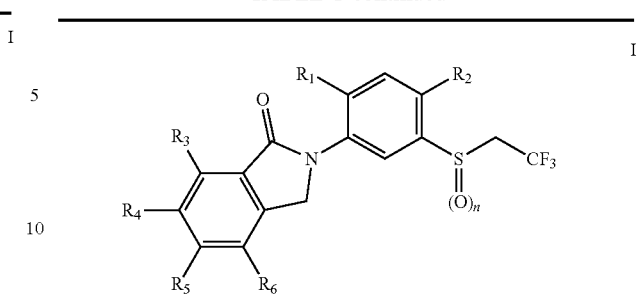

| No. | $R_1$ | $R_2$ | $R_3$ | $R_4$ | $R_5$ | $R_6$ | n |
|---|---|---|---|---|---|---|---|
| 170 | F | Me | H | Br | H | H | 1 |
| 171 | Cl | Me | H | Br | H | H | 0 |
| 172 | Cl | Me | H | Br | H | H | 1 |
| 173 | Br | Me | H | Br | H | H | 0 |
| 174 | Br | Me | H | Br | H | H | 1 |
| 175 | Me | Me | H | Br | H | H | 0 |
| 176 | Me | Me | H | Br | H | H | 1 |
| 177 | CN | Me | H | Br | H | H | 0 |
| 178 | CN | Me | H | Br | H | H | 1 |
| 179 | F | F | H | Br | H | H | 0 |
| 180 | F | F | H | Br | H | H | 1 |
| 181 | F | Cl | H | Br | H | H | 0 |
| 182 | F | Cl | H | Br | H | H | 1 |
| 183 | F | CN | H | Br | H | H | 0 |
| 184 | F | CN | H | Br | H | H | 1 |
| 185 | Cl | CN | H | Br | H | H | 0 |
| 186 | Cl | CN | H | Br | H | H | 1 |
| 187 | Br | CN | H | Br | H | H | 0 |
| 188 | Br | CN | H | Br | H | H | 1 |
| 189 | Cl | Cl | H | Br | H | H | 0 |
| 190 | Cl | Cl | H | Br | H | H | 1 |
| 191 | Br | Br | H | Br | H | H | 0 |
| 192 | Br | Br | H | Br | H | H | 1 |
| 193 | F | Me | H | H | Br | H | 0 |
| 194 | F | Me | H | H | Br | H | 1 |
| 195 | Cl | Me | H | H | Br | H | 0 |
| 196 | Cl | Me | H | H | Br | H | 1 |
| 197 | Br | Me | H | H | Br | H | 0 |
| 198 | Br | Me | H | H | Br | H | 1 |
| 199 | Me | Me | H | H | Br | H | 0 |
| 200 | Me | Me | H | H | Br | H | 1 |
| 201 | CN | Me | H | H | Br | H | 0 |
| 202 | CN | Me | H | H | Br | H | 1 |
| 203 | F | F | H | H | Br | H | 0 |
| 204 | F | F | H | H | Br | H | 1 |
| 205 | F | Cl | H | H | Br | H | 0 |
| 206 | F | Cl | H | H | Br | H | 1 |
| 207 | F | CN | H | H | Br | H | 0 |
| 208 | F | CN | H | H | Br | H | 1 |
| 209 | Cl | CN | H | H | Br | H | 0 |
| 210 | Cl | CN | H | H | Br | H | 1 |
| 211 | Br | CN | H | H | Br | H | 0 |
| 212 | Br | CN | H | H | Br | H | 1 |
| 213 | Cl | Cl | H | H | Br | H | 0 |
| 214 | Cl | Cl | H | H | Br | H | 1 |
| 215 | Br | Br | H | H | Br | H | 0 |
| 216 | Br | Br | H | H | Br | H | 1 |

TABLE 2

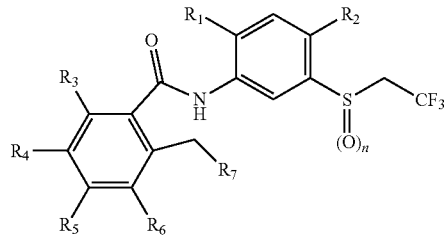

| No. | $R_1$ | $R_2$ | $R_3$ | $R_4$ | $R_5$ | $R_6$ | $R_7$ | n |
|---|---|---|---|---|---|---|---|---|
| II.1 | F | Me | H | H | H | H | Cl | 0 |
| II.2 | F | Me | H | H | H | H | Cl | 1 |
| II.3 | Cl | Me | H | H | H | H | Cl | 0 |
| II.4 | Cl | Me | H | H | H | H | Cl | 1 |
| II.5 | Br | Me | H | H | H | H | Cl | 0 |
| II.6 | Br | Me | H | H | H | H | Cl | 1 |
| II.7 | Me | Me | H | H | H | H | Cl | 0 |
| II.8 | Me | Me | H | H | H | H | Cl | 1 |
| II.9 | CN | Me | H | H | H | H | Cl | 0 |
| II.10 | CN | Me | H | H | H | H | Cl | 1 |
| II.11 | F | F | H | H | H | H | Cl | 0 |
| II.12 | F | F | H | H | H | H | Cl | 1 |
| II.13 | F | Cl | H | H | H | H | Cl | 0 |
| II.14 | F | Cl | H | H | H | H | Cl | 1 |
| II.15 | F | CN | H | H | H | H | Cl | 0 |
| II.16 | F | CN | H | H | H | H | Cl | 1 |
| II.17 | Cl | CN | H | H | H | H | Cl | 0 |
| II.18 | Cl | CN | H | H | H | H | Cl | 1 |
| II.19 | Br | CN | H | H | H | H | Cl | 0 |
| II.20 | Br | CN | H | H | H | H | Cl | 1 |
| II.21 | Cl | Cl | H | H | H | H | Cl | 0 |
| II.22 | Cl | Cl | H | H | H | H | Cl | 1 |
| II.23 | Br | Br | H | H | H | H | Cl | 0 |
| II.24 | Br | Br | H | H | H | H | Cl | 1 |
| II.25 | F | Me | H | H | H | H | Br | 0 |
| II.26 | F | Me | H | H | H | H | Br | 1 |
| II.27 | Cl | Me | H | H | H | H | Br | 0 |
| II.28 | Cl | Me | H | H | H | H | Br | 1 |
| II.29 | Br | Me | H | H | H | H | Br | 0 |
| II.30 | Br | Me | H | H | H | H | Br | 1 |
| II.31 | Me | Me | H | H | H | H | Br | 0 |
| II.32 | Me | Me | H | H | H | H | Br | 1 |
| II.33 | CN | Me | H | H | H | H | Br | 0 |
| II.34 | CN | Me | H | H | H | H | Br | 1 |
| II.35 | F | F | H | H | H | H | Br | 0 |
| II.36 | F | F | H | H | H | H | Br | 1 |
| II.37 | F | Cl | H | H | H | H | Br | 0 |
| II.38 | F | Cl | H | H | H | H | Br | 1 |
| II.39 | F | CN | H | H | H | H | Br | 0 |
| II.40 | F | CN | H | H | H | H | Br | 1 |
| II.41 | Cl | CN | H | H | H | H | Br | 0 |
| II.42 | Cl | CN | H | H | H | H | Br | 1 |
| II.43 | Br | CN | H | H | H | H | Br | 0 |
| II.44 | Br | CN | H | H | H | H | Br | 1 |
| II.45 | Cl | Cl | H | H | H | H | Br | 0 |
| II.46 | Cl | Cl | H | H | H | H | Br | 1 |
| II.47 | Br | Br | H | H | H | H | Br | 0 |
| II.48 | Br | Br | H | H | H | H | Br | 1 |
| II.49 | F | Me | H | F | H | H | Cl | 0 |
| II.50 | F | Me | H | F | H | H | Cl | 1 |
| II.51 | F | Me | H | Cl | H | H | Cl | 0 |
| II.52 | F | Me | H | Cl | H | H | Cl | 1 |
| II.53 | F | Me | H | Br | H | H | Cl | 0 |
| II.54 | F | Me | H | Br | H | H | Cl | 1 |
| II.55 | F | Me | H | CN | H | H | Cl | 0 |
| II.56 | F | Me | H | CN | H | H | Cl | 1 |
| II.57 | F | Me | H | H | F | H | Cl | 0 |
| II.58 | F | Me | H | H | F | H | Cl | 1 |
| II.59 | F | Me | H | H | Cl | H | Cl | 0 |
| II.60 | F | Me | H | H | Cl | H | Cl | 1 |
| II.61 | F | Me | H | H | Br | H | Cl | 0 |
| II.62 | F | Me | H | H | Br | H | Cl | 1 |
| II.63 | F | Me | H | H | CN | H | Cl | 0 |
| II.64 | F | Me | H | H | CN | H | Cl | 1 |
| II.65 | F | Me | H | F | H | H | Br | 0 |
| II.66 | F | Me | H | F | H | H | Br | 1 |
| II.67 | F | Me | H | Cl | H | H | Br | 0 |
| II.68 | F | Me | H | Cl | H | H | Br | 1 |
| II.69 | F | Me | H | Br | H | H | Br | 0 |
| II.70 | F | Me | H | Br | H | H | Br | 1 |
| II.71 | F | Me | H | CN | H | H | Br | 0 |
| II.72 | F | Me | H | CN | H | H | Br | 1 |
| II.73 | F | Me | H | H | F | H | Br | 0 |
| II.74 | F | Me | H | H | F | H | Br | 1 |
| II.75 | F | Me | H | H | Cl | H | Br | 0 |
| II.76 | F | Me | H | H | Cl | H | Br | 1 |
| II.77 | F | Me | H | H | Br | H | Br | 0 |
| II.78 | F | Me | H | H | Br | H | Br | 1 |
| II.79 | F | Me | H | H | CN | H | Br | 0 |
| II.80 | F | Me | H | H | CN | H | Br | 1 |

Compounds of the general formula I of the present invention can be prepared according to the following solution, unless otherwise indicated, the definitions of groups in the formula are the same as aforementioned (G=$R_7$=Cl or Br).

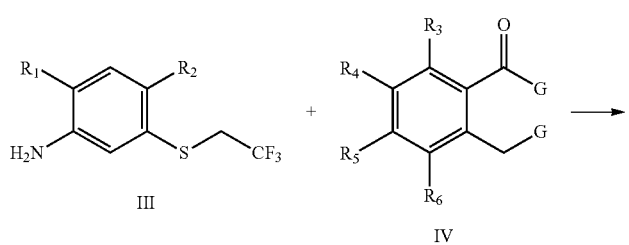

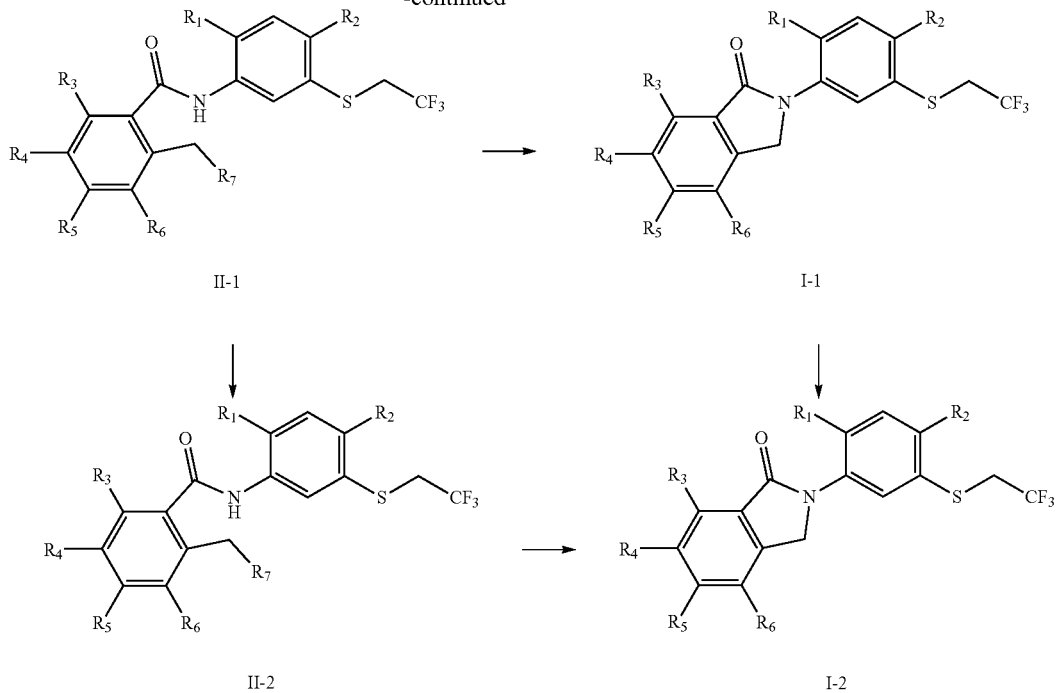

Compounds of general formula III and compounds of general formula IV react in a suitable solvent at a temperature from −10° C. to the boiling point of the solvent for 0.5-48 hours to prepare intermediate compounds of general formula II-1; the reaction can be carried out in the presence or absence of alkali; suitable solvents can be aromatic hydrocarbons such as benzene, toluene and xylene, ketones such as acetone, methyl ethyl ketone and methyl isobutyl ketone, halogenated hydrocarbons such as chloroform and dichloromethane, esters such as methyl acetate and ethyl acetate, ethers such as tetrahydrofuran, dioxane, diethyl ether and 1, 2-dimethoxyethane, polar solvents such as water, acetonitrile, N, N-dimethyl formamide and N-methyl pyrrolidone, or mixtures thereof above; suitable bases are preferably selected from organic bases such as triethylamine, pyridine, DBU and 4-dimethylaminopyridine.

The intermediate compound of the general formula II-1 (n=0) reacts with a suitable oxidizing reagent to prepare a corresponding sulfoxide compound, namely the intermediate compound of the general formula II-2 (n=1); the suitable oxidizing reagent may be m-chloroperoxybenzoic acid, hydrogen peroxide or sodium (meta) periodate. The reaction solvent is selected from water, methanol, ethanol, ether, dichloromethane, chloroform, carbon tetrachloride, hexane, benzene, toluene, ethyl acetate, DMF, tetrahydrofuran or dioxane, etc. The reaction is usually carried out at 0-100° C. The reaction time is usually from 10 minutes to 48 hours.

The intermediate compound of the general formula II-1 reacts in a suitable solvent in the presence of a suitable base at a temperature from −10° C. to the boiling point of the solvent for 0.5-48 hours to prepare the compound of the general formula I-1; similarly, the intermediate compound of the general formula II-2 can react in a suitable solvent in the presence of a suitable base at a temperature from −10° C. to the boiling point of the solvent for 0.5-48 hours to prepare the compound of the general formula I-2; suitable solvents may be aromatic hydrocarbons such as benzene, toluene and xylene, ketones such as acetone, methyl ethyl ketone and methyl isobutyl ketone, halogenated hydrocarbons such as chloroform and dichloromethane, esters such as methyl acetate and ethyl acetate, ethers such as tetrahydrofuran, dioxane, diethyl ether and 1, 2-dimethoxyethane, polar solvents such as water, acetonitrile, N, N-dimethylformamide and N-methyl pyrrolidone, or mixtures thereof above; suitable bases are preferably selected from organic bases such as triethylamine, pyridine, DBU and 4-dimethylaminopyridine.

The compound of the general formula I-1 (n=0) reacts with a suitable oxidizing reagent to prepare a corresponding sulfoxide compound, namely the compound of general formula I-2 (n=1); the suitable oxidizing reagent can be m-chloroperoxybenzoic acid, hydrogen peroxide or sodium (meta) periodate. The reaction solvent is selected from water, methanol, ethanol, ether, dichloromethane, chloroform, carbon tetrachloride, hexane, benzene, toluene, ethyl acetate, DMF, tetrahydrofuran or dioxane, etc. The reaction is usually carried out at 0-100° C. The reaction time is usually from 10 min to 48 h.

Compounds of the general formula III can be prepared by referring to methods reported in WO2010100189, US2012053052, JP2012519662, EP2403837, CN102341376, WO201392350, WO2013157229, WO2007131680, WO2015036377, WO2013030319, WO2013030262, WO2013030338, WO2018015852, WO2014202510, WO2014202505 or WO2015004028.

Compounds of the general formula IV can be prepared by referring to methods reported in WO2008023810, CN101139308, WO2001042185, WO2001042182, WO2001042183, WO9916743, WO2004011450, CN105153013, WO2002060886, WO20160194285, WO2014014835 or Journal of Heterocyclic Chemistry, 52(4), 1136-1142; 2015.

As the compound of the general formula I of the present invention has unexpectedly high acaricidal activity, the technical solution of the present invention also includes the use of the compound of the general formula I for preparing acaricides in agriculture or other fields. Especially, the compounds of the general formula I are active against important varieties of the following families (the listed objects are only used to illustrate the invention, but in no way limit the invention): tetranychidae (*Tetranychus urticae, Tetranychus cinnabarinus, Panonychus ulmi, Tetranychus citri,* kanzawa spider mite, *Tetranychus viennensis* zacher, etc.), eriophyidae, tarsonemidae, eupodidae, tenuipalpidae, etc.

Because of their positive characteristics, the above compounds can be advantageously used to protect important crops, domestic animals and breeding stocks in agriculture and horticulture, as well as the environment frequented by human beings from pest mites.

In order to obtain the desired effect, the dosage of the compound varies due to various factors, such as the compound used, the crops to be protected, the type of harmful organisms, the degree of infection, the climatic conditions, the application methods, the dosage forms adopted.

The compound dose of 10 g to 5 kg per hectare can provide adequate prevention and control.

The present invention also includes an acaricidal composition with the compound of the general formula I as an active component, and wherein the active component comprises from 0.1 to 99% by weight of the acaricidal composition. The acaricidal composition also includes carriers acceptable in the fields of agriculture, forestry and hygiene.

The composition of the present invention can be administered in the preparation form. Compounds of the general formula I as active components are dissolved or dispersed in carriers or prepared into preparations so as to be more easily dispersed when used as acaricides. For example, these chemical preparations can be made into wettable powder, oil suspension, aqueous suspension, aqueous emulsion, aqueous solution or emulsifiable concentrate, etc. In these compositions, at least one liquid or solid carrier is added, and an appropriate surfactant can be added when necessary.

The technical solution of the invention also comprises a method for preventing and controlling pest mites: The acaricidal composition of the present invention is applied to the pest mites or their growth medium. Generally, the suitable effective amount is 10 g to 1000 g per hectare, and the preferred effective amount is 20 to 500 grams per hectare.

For some applications, for example in agriculture, one or more other fungicides, insecticides and acaricides, herbicides, plant growth regulators, fertilizers, etc. can be added to the acaricidal composition of the present invention, thereby producing additional advantages and effects.

It should be clear that various transformations and modifications can be made within the scope defined by the claims of the present invention.

DETAILED DESCRIPTION OF THE INVENTION

The following specific examples serve to further illustrate the present invention, but the present invention is by no means limited to these examples. (Unless otherwise specified, all raw materials used are commercially available)

EXAMPLES OF SYNTHESIS

According to the synthetic route described above, the compound shown in general formula I and the compound shown in the intermediate general formula II of the present invention can be respectively prepared by using different raw material compounds, which are further described in detail as follows:

Example 1: Preparation of Intermediate Compound II.1

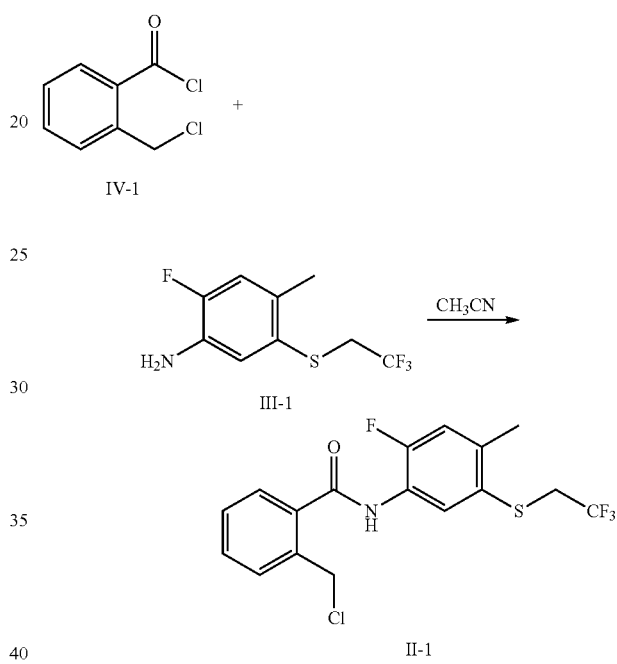

In an ice bath, 3.20 g (13.39 mmol) of 3-(2,2,2-trifluoroethylthio)-4-methyl-6-fluoroaniline (intermediate III-1, obtained by the methods reported in WO2010100189, US2012053052, JP2012519662, EP2403837 or CN102341376, etc.) was weighed into a 100 ml three-necked flask, 30 ml of acetonitrile was added and stirred; 2.76 g of (14.68 mmol) 2-(chloromethyl) benzoyl chloride (intermediate IV-1, obtained by the methods reported in WO2008023810, CN101139308, WO2001042185, WO2001042182, WO2001042183, WO9916743, and the like) in 20 ml of acetonitrile was slowly added dropwise to the above solution; after addition, the temperature was raised to the room temperature, and the reaction was continued for 5 hours; after completion of the TLC monitoring reaction, desolvation under reduced pressure was performed and residues were subjected to column chromatography (with an eluent being ethyl acetate and petroleum ether in a volume ratio of 1:30) to obtain 4.71 g of white solid, i.e., the intermediate compound II.1.

Characterization data are as follows: $^1$H NMR (600 MHz, internal standard TMS, solvent CDCl$_3$) δ (ppm): 8.65 (d, 1H), 7.86 (s, 1H), 7.62 (d, 1H), 7.57-7.50 (m, 2H), 7.45 (t, 1H), 7.02 (d, 1H), 4.89 (s, 2H), 3.44 (q, 2H), 2.46 (s, 3H). LC-MS (m/z, ESI): 392.1 (m+H), 414.0 (m+Na).

Example 2: Preparation of Intermediate Compound II.2

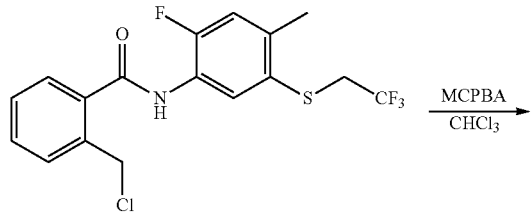

II-1

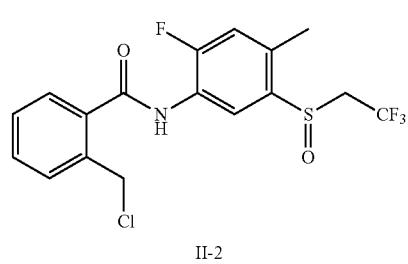

II-2

1.00 g (2.56 mmol) of intermediate compound II.1 was dissolved in 50 ml chloroform, and the temperature was reduced to 0-5° C. At this temperature, 0.55 g (2.71 mmol, purity of 85%) of m-chloroperoxybenzoic acid was added for three times. The reaction mixture was stirred at 0-5° C. for 1 hour. After completion of the TLC monitoring reaction, the reaction solution was washed with an aqueous solution of sodium thiosulfate and an aqueous solution of sodium bicarbonate sequentially, dried with anhydrous magnesium sulfate, filtered, and desolventized under reduced pressure, and the resulting solid was recrystallized in methanol to obtain 0.89 g of a white solid, i.e., the intermediate compound II.2.

Characterization data are as follows: $^1$H NMR (600 MHz, internal standard TMS, solvent CDCl$_3$) δ (ppm): 8.98 (d, 1H), 7.96 (s, 1H), 7.64-7.60 (m, 1H), 7.58-7.51 (m, 2H), 7.46 (td, 1H), 7.07 (d, 1H), 4.92 (d, 1H), 4.87 (d, 1H), 3.69-3.57 (m, 1H), 3.53-3.40 (m, 1H), 2.43 (s, 3H). LC-MS (m/z, ESI): 408.0 (m+H), 430.0 (m+Na).

Example 3: Preparation of Compound 1

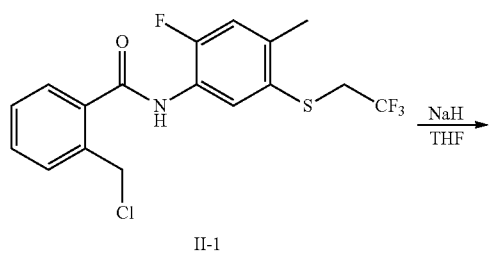

II-1

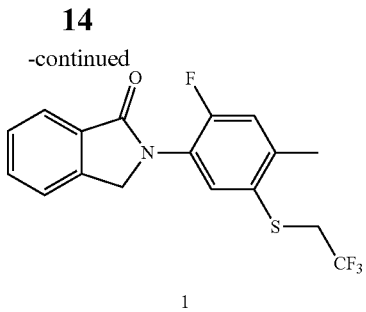

1

0.15 g (3.75 mmol) of sodium hydride (60% purity) was weighed into a reaction bottle, and 30 ml of tetrahydrofuran and 1.00 g (2.56 mmol) of intermediate compound II.1 were sequentially added, and stirred in an ice bath; the reaction solution was heated to the reflux reaction for 10 hours after no bubbles emerge; after completion of the TLC monitoring reaction, an appropriate amount of water was added to quench the reaction; ethyl acetate was added for extraction, the organic layer was sequentially washed with saturated saline solution, dried with anhydrous magnesium sulfate, filtered, and desolventized under reduced pressure, and residues were purified by column chromatography (with the eluent being ethyl acetate and petroleum ether in a volume ratio of 1:20) to obtain 0.34 g of white solid, namely the compound 1.

Characterization data are as follows: $^1$H NMR (600 MHz, internal standard TMS, solvent CDCl$_3$) δ (ppm): 7.95 (d, 1H), 7.85 (d, 1H), 7.62 (td, 1H), 7.55-7.50 (m, 2H), 7.10 (d, 1H), 4.86 (s, 2H), 3.39 (q, 2H), 2.50 (s, 3H). LC-MS (m/z, ESI): 356.1 (m+H), 378.1 (m+Na).

Example 4: Preparation of Compound 2

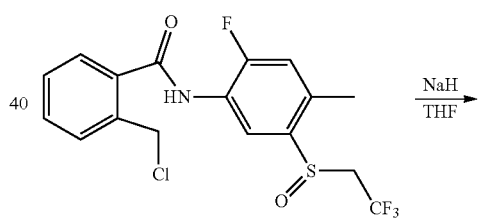

II.2

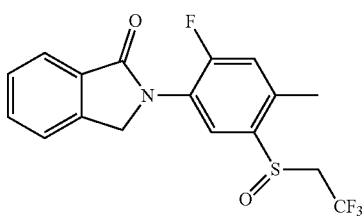

2

The method for preparing compound 2 from intermediate compound II.2 is the same as that in example 3.

Characterization data are as follows: $^1$H NMR (600 MHz, internal standard TMS, solvent CDCl$_3$) δ (ppm): 8.23 (d, 1H), 7.96 (dt, 1H), 7.64 (td, 1H), 7.57-7.51 (m, 2H), 7.14 (d, 1H), 4.96 (d, 1H), 4.80 (d, 1H), 3.60-3.41 (m, 2H), 2.44 (s, 3H). LC-MS (m/z, ESI): 372.1 (m+H), 394.0 (m+Na).

With reference to the above examples, other compounds in general formula I and general formula II of the present invention can be prepared.

Physical property data, NMR data and MS data of some compounds are as follows:

intermediate compound II.63: white solid. $^1$H NMR (600 MHz, internal standard TMS, solvent CDCl$_3$) δ(ppm): 8.58 (d, 1H), 7.87 (d, 1H), 7.82 (s, 1H), 7.77-7.70 (m, 2H), 7.05 (d, 1H), 4.86 (s, 2H), 3.43 (q, 2H), 2.47 (s, 3H). LC-MS (m/z, ESI): 417.1 (m+H).

intermediate compound II.64: white solid. $^1$H NMR (600 MHz, internal standard TMS, solvent CDCl$_3$) δ(ppm): 8.91 (d, 1H), 7.98 (s, 1H), 7.87 (d, 1H), 7.79-7.70 (m, 2H), 7.10 (d, 1H), 4.88 (d, 1H), 4.84 (d, 1H), 3.61 (dq, 1H), 3.45 (dq, 1H), 2.43 (s, 3H). LC-MS (m/z, ESI): 433.1 (m+H).

compound 97: white solid. $^1$H NMR (600 MHz, internal standard TMS, solvent CDCl$_3$) δ(ppm): 8.06 (d, 1H), 7.85-7.81 (m, 3H), 7.12 (d, 1H), 4.92 (s, 2H), 3.38 (q, 2H), 2.51 (s, 3H). LC-MS (m/z, ESI): 381.1 (m+H).

compound 98: white solid. $^1$H NMR (600 MHz, internal standard TMS, solvent CDC) δ(ppm): 8.22 (d, 1H), 8.06 (d, 1H), 7.87-7.83 (m, 2H), 7.17 (d, 1H), 5.02 (d, 1H), 4.86 (d, 1H), 3.59-3.42 (m, 2H), 2.45 (s, 3H). LC-MS (m/z, ESI): 397.1 (m+H).

Example of Preparations

Example 5: Preparation of 5% Compound 1 Microcapsule Suspension

According to the formula requirements, 5 parts of compound 1, 5 parts of 600 #, 10 parts of xylene and 1 part of diphenylmethane diisocyanate were evenly stirred to prepare an oil phase, which was then added into an aqueous phase consisting of 1 part of ethylenediamine, 5 parts of glycerol, 3 parts of Atlox 4913, 2 parts of EFW, 1 part of SAG1522 and the balance water, and then high-speed stirring, curing and heat preservation were performed to obtain a 5% compound 1 microcapsule suspension.

Example 6: Preparation of 10% Compound 1 Emulsifiable Concentrate

According to the formula requirements, 10 parts of compound 1, 5 parts of 0201B, 7 parts of 0203B and solvent oil 150 to make up to 100% were added into a mixing kettle, stirred and mixed evenly, and heated to be dissolved in a hot water bath when necessary, to obtain a 10% compound 1 emulsifiable concentrate.

Example 7: Preparation of 15% Compound 1 Aqueous Emulsion

According to the formula requirements, 15 parts of compound 1, 8 parts of T-20, 4 parts of pesticide emulsifier S-85, 5 parts of tributyl phosphate and 5 parts of solvent oil 200 were added into a mixing kettle, stirred and mixed to be dissolved into a uniform oil phase, and the balance water (which was supplemented to be 100%) was added into the oil phase under high-speed stirring to obtain a 15% compound 1 aqueous emulsion with good dispersibility.

Example 8: Preparation of 15% Compound 1 Dispersible Oil Suspension

According to the formula requirements, 15 parts of compound 1, 6 parts of dispersant SP-OF3468, 6 parts of dispersant SP-OF3472, 2 parts of pesticide emulsifier 1601 #, 2 parts of organic bentonite and methyl oleate to make up to 100% were sequentially added into a mixing tank for mixing, coarsely ground and homogenized by high shear, and then pumped into a sand mill for fine grinding, the particle size of sanded materials was detected by a particle size analyzer, and when the particle size reached the standard requirement, filtering was performed to obtain a 15% compound 1 dispersible oil suspension.

Example 9: Preparation of 60% Compound 1 Water Dispersible Granules

According to the formula requirements, 60 parts of compound 1, 2 parts of Morwet EFW, 4 parts of dispersant D425, 4 parts of alkyl naphthalene sulfonate formaldehyde condensate, 10 parts of soluble starch, 8 parts of ammonium sulfate and diatomite to make up to 100% were added together, mixed and ground, kneaded with water, and then added into a granulator equipped with a screen of a certain size for granulation. Then, after drying and sieving (according to the screen range), 60% compound 1 water dispersible granules were obtained.

Example 10: Preparation of 50% Compound 1 Wettable Powder

According to the formula requirements, 50 parts of compound 1, 3 parts of sodium dodecyl sulfate, 4 parts of alkyl naphthalene sulfonic acid condensation polymer sodium salt, 4 parts of sodium methylene naphthalene sulfonate, 4 parts of sodium lignosulfonate, 5 parts of white carbon black and diatomite to make up to 100% were thoroughly mixed, and ground by an ultrafine grinder to obtain 50% compound 1 wettable powder.

Example 11: Preparation of 10% Compound 1 Microemulsion

According to the formula requirements, 10 parts of compound 1, 6 parts of pesticide emulsifier 0201B, 2 parts of NP-15, 8 parts of YUS-A51G, 5 parts of methanol and 5 parts of cyclohexanone were added together and dissolved to be a uniform oil phase, and the balance was supplemented to be 100% with water. Under high-speed stirring, the water phase was added to the oil phase or the oil phase was added to the water phase to form a 10% compound 1 microemulsion with good dispersibility.

Example 12: Preparation of 10% Compound 1 Soluble Concentrate

According to the formula requirements, 10 parts of compound 1, 6 parts of tristyrylphenol polyoxyethylene(n20) ether phosphorylated triethanolamine salt, 3 parts of pesticide emulsifier T-20, 2 parts of pesticide emulsifier 0201B, 3 parts of N-methyl pyrrolidone and cyclohexanone to make up to 100% were mixed evenly, and heated to be dissolved in a hot water bath when necessary, to obtain a 10% compound 1 soluble concentrate.

Example 13: Preparation of 15% Compound 1 Emulsifiable Powder

According to the formula requirements, 15 parts of compound 1, 2 parts of pesticide emulsifier 1601 #, 3 parts of 500 #, 5 parts of pesticide emulsifier 0201B, 5 parts of N-methyl pyrrolidone and 5 parts of Armid FMPC were added into a mixing kettle, stirred and mixed evenly, and heated to be dissolved in a hot water bath when necessary, and the above oil base was uniformly sprayed onto a mixture composed of 20 parts of white carbon black and bentonite to make up to 100% under stirring, and then the mixture was ground by an ultrafine grinder to obtain 15% compound 1 emulsifiable powder.

Example 14: Preparation of 20% Compound 1 Suspension

According to the formula requirements, 20 parts of compound 1, 2 parts of dispersant 4913, 2 parts of wetting agent TXC, 2 parts of pesticide emulsifier 1601 #, 2 parts of white carbon black, 0.2 parts of xanthan gum, 1 part of SAG1522, 5 parts of ethylene glycol and water to make up to 100% were sequentially added into a mixing tank, coarsely ground and homogenized by high shear, and then pumped into a sand mill for fine grinding, the particle size of sanded materials was detected by a particle size analyzer, and when the particle size reached the standard requirement, filtering was performed to obtain a 20% compound 1 suspension.

Example 15: Preparation of 50% Compound 1 Dry Suspension

According to the formula requirements, 50 parts of compound 1, 20 parts of sodium lignosulfonate, 2 parts of wetting agent TXC, 2 parts of white carbon black and kaolin to make up to 100% were sequentially added into a mixing tank and mixed with water, coarsely ground and homogenized by high shear, and then pumped into a sand mill for fine grinding, the particle size of sanded materials was detected by a particle size analyzer, and spray granulation and drying were performed to obtain a 50% compound 1 dry suspension.

Example 16: Preparation of 10% Compound 1 Ultra-Low Volume Agent

According to the formula requirements, 10 parts of compound 1, 5 parts of Armid FMPC, 2 parts of pesticide emulsifier 0201B, 1 part of S-80 and solvent oil to make up to 100% were added into a mixing kettle, stirred and mixed evenly, and heated to be dissolved in a hot water bath when necessary, to obtain pesticide emulsifier 10% compound 1 ultra-low volume agent.

Example 17: Preparation of 10% Compound 1 Suspension Seed Coating

According to the formula requirements, 10 parts of compound 1, 2 parts of dispersant FS3000, 2 parts of wetting agent TXC, 2 parts of SK-92FS1, 2 parts of white carbon black, 0.2 parts of xanthan gum, 10 parts of 10% polyvinyl alcohol solution, 0.2 parts of alkaline rose essence, 1 part of SAG1522, 5 parts of ethylene glycol and water to make up to 100% were sequentially added into a mixing tank for mixing, coarsely ground and homogenized by high shear, and then pumped into a sand mill for fine grinding, the particle size of sanded materials was detected by a particle size analyzer, and when the particle size reached the standard requirement, filtering was performed to obtain a 10% compound 1 suspension seed coating.

Example 18: Preparation of 30% Compound 1 Powder

According to the formula requirements, 30 parts of compound 1, 5 parts of sodium methylene naphthalene sulfonate, 6 parts of sodium lignosulfonate, 8 parts of white carbon black and diatomite to make up to 100% were thoroughly mixed, and ground by an ultrafine grinder to obtain 30% compound 1 powder.

Example 19: Preparation of 50% Compound 1 Soluble Powder

According to the formula requirements, 50 parts of compound 1, 3 parts of sodium dodecyl sulfate, 4 parts of sodium salt of alkyl naphthalene sulfonic acid polycondensate, 4 parts of EFW 5 parts of hydroxypropyl cellulose and ammonium sulfate to make up to 100% were thoroughly mixed, and ground by an ultrafine grinder to obtain 50% compound 1 soluble powder.

Example 20: Preparation of 10% Compound 1 Tablets

According to the formula requirements, 10 parts of compound 1, 2 parts of sodium methyl naphthalene sulfonate-formaldehyde condensate, 1 part of sodium dodecyl sulfate, 15 parts of soluble starch, 8 parts of sodium sulfate, 5 parts of white carbon black and diatomite to make up to 100% were thoroughly mixed, ground by an ultrafine grinder and then tabletted to obtain 10% compound 1 tablets.

Example 21: Preparation of 5% Compound 2 Microcapsule Suspension

According to the formula requirements, 5 parts of compound 2, 5 parts of 600 #, 10 parts of xylene and 1 part of diphenylmethane diisocyanate were evenly stirred to prepare an oil phase, which was then added into an aqueous phase consisting of 1 part of ethylenediamine, 5 parts of glycerol, 3 parts of Atlox 4913, 2 parts of EFW 1 part of SAG1522 and the balance of water, and then high-speed stirring, curing and heat preservation were performed to obtain a 5% compound 2 microcapsule suspension.

Example 22: Preparation of 10% Compound 2 Emulsifiable Concentrate

According to the formula requirements, 10 parts of compound 2, 5 parts of 0201B, 7 parts of 0203B and solvent oil 150 to make up to 100% were added into a mixing kettle, stirred and mixed evenly, and heated to be dissolved in a hot water bath when necessary to obtain a 10% compound 2 emulsifiable concentrate.

Example 23: Preparation of 15% Compound 2 Aqueous Emulsion

According to the formula requirements, 15 parts of compound 2, 8 parts of T-20, 4 parts of pesticide emulsifier S-85, 5 parts of tributyl phosphate and 5 parts of solvent oil 200 were added into a mixing kettle, stirred and mixed to be dissolved into a uniform oil phase, and the balance of water to make up to 100% was added into the oil phase under high-speed stirring to obtain a 15% compound 2 emulsion in water with good dispersibility.

Example 24: Preparation of 15% Compound 2 Dispersible Oil Suspension

According to the formula requirements, 15 parts of compound 2, 6 parts of dispersant SP-OF3468, 6 parts of dispersant SP-OF3472, 2 parts of pesticide emulsifier 1601 #, 2 parts of organic bentonite and methyl oleate to make up to 100% were sequentially added into a mixing tank for mixing, coarsely ground and homogenized by high shear, and then pumped into a sand mill for fine grinding, the particle size of sanded materials was detected by a particle size analyzer, and when the particle size reached the standard requirement, filtering was performed to obtain a 15% compound 2 dispersible oil suspension.

Example 25: Preparation of 60% Compound 2 Water Dispersible Granules

According to the formula requirements, 60 parts of compound 2, 2 parts of Morwet EFW, 4 parts of dispersant D425, 4 parts of alkyl naphthalene sulfonate-formaldehyde condensate, 10 parts of soluble starch, 8 parts of ammonium sulfate and diatomite to make up to 100% were added together, mixed and ground, kneaded with water, and then added into a granulator equipped with a screen of a certain size for granulation. Then, after drying and sieving (according to the screen range), 60% compound 2 water dispersible granules were obtained.

Example 26: Preparation of 50% Compound 2 Wettable Powder

According to the formula requirements, 50 parts of compound 2, 3 parts of sodium dodecyl sulfate, 4 parts of sodium salt of alkyl naphthalene sulfonic acid polycondensate, 4 parts of sodium methylene naphthalene sulfonate, 4 parts of sodium lignosulfonate, 5 parts of white carbon black and diatomite to make up to 100% were thoroughly mixed, and ground by an ultrafine grinder to obtain 50% compound 2 wettable powder

Example 27: Preparation of 10% Compound 2 Microemulsion

According to the formula requirements, 10 parts of compound 2, 6 parts of pesticide emulsifier 0201B, 2 parts of NP-15, 8 parts of YUS-A51G, 5 parts of methanol and 5 parts of cyclohexanone were added together and dissolved to be a uniform oil phase, and the balance was supplemented to be 100% with water. Under high-speed stirring, the water phase was added to the oil phase or the oil phase was added to the water phase to form a 10% compound 2 microemulsion with good dispersibility.

Example 28: Preparation of 10% Compound 2 Soluble Concentrate

According to the formula requirements, 10 parts of compound 2, 6 parts of tristyrylphenol polyoxyethylene(n20) ether phosphorylated triethanolamine salt, 3 parts of pesticide emulsifier T-20, 2 parts of pesticide emulsifier 0201B, 3 parts of N-methyl pyrrolidone and cyclohexanone to make up to 100% were mixed evenly, and heated to be dissolved in a hot water bath when necessary, to obtain a 10% compound 2 soluble concentrate.

Example 29: Preparation of 15% Compound 2 Emulsifiable Powder

According to the formula requirements, 15 parts of compound 2, 2 parts of pesticide emulsifier 1601 #, 3 parts of 500 #, 5 parts of pesticide emulsifier 0201B, 5 parts of N-methyl pyrrolidone and 5 parts of Armid FMPC were added into a mixing kettle, stirred and mixed evenly, and heated to be dissolved in a hot water bath when necessary, and the above oil base was uniformly sprayed onto a mixture composed of 20 parts of white carbon black and bentonite to make up to 100% under stirring, and then ground by an ultrafine grinder to obtain 15% compound 2 emulsifiable powder.

Example 30: Preparation of 20% Compound 2 Suspension

According to the formula requirements, 20 parts of compound 2, 2 parts of dispersant 4913, 2 parts of wetting agent TXC, 2 parts of pesticide emulsifier 1601 #, 2 parts of white carbon black, 0.2 parts of xanthan gum, 1 part of SAG1522, 5 parts of ethylene glycol and water to make up to 100% were sequentially added into a mixing tank for mixing, coarsely ground and homogenized by high shear, and then pumped into a sand mill for fine grinding, the particle size of sanded materials was detected by a particle size analyzer, and when the particle size reached the standard requirement, filtering was performed to obtain a 20% compound 2 suspension.

Example 31: Preparation of 50% Compound 2 Dry Suspension

According to the formula requirements, 50 parts of compound 2, 20 parts of sodium lignosulfonate, 2 parts of wetting agent TXC, 2 parts of white carbon black and kaolin to make up to 100% were sequentially added into a mixing tank and mixed with water, coarsely ground and homogenized by high shear, and then pumped into a sand mill for fine grinding, the particle size of sanded materials was detected by a particle size analyzer, and spray granulation and drying were performed to obtain a 50% compound 2 dry suspension.

Example 32: Preparation of 10% Compound 2 Ultra-Low Volume Agent

According to the formula requirements, 10 parts of compound 2, 5 parts of Armid FMPC, 2 parts of pesticide emulsifier 0201B, 1 part of S-80 and solvent oil to make up to 100% were added into a mixing kettle, stirred and mixed evenly, and heated to be dissolved in a hot water bath when necessary, to obtain a 10% compound 2 ultra-low volume agent.

Example 33: Preparation of 10% Compound 2 Suspension Seed Coating

According to the formula requirements, 10 parts of compound 2, 2 parts of dispersant FS3000, 2 parts of wetting agent TXC, 2 parts of SK-92FS1, 2 parts of white carbon black, 0.2 parts of xanthan gum, 10 parts of 10% polyvinyl alcohol solution, 0.2 parts of alkaline rose essence, 1 part of SAG1522, 5 parts of ethylene glycol and water to make up to 100% were sequentially added into a mixing tank for mixing, coarsely ground and homogenized by high shear, and then pumped into a sand mill for fine grinding, the particle size of sanded materials was detected by a particle size analyzer, and when the particle size reached the standard requirement, filtering was performed to obtain a 10% compound 2 suspension seed coating.

Example 34: Preparation of 30% Compound 2 Powder

According to the formula requirements, 30 parts of compound 2, 5 parts of sodium methylene naphthalene sulfonate, 6 parts of sodium lignosulfonate, 8 parts of white carbon black and diatomite to make up to 100% were thoroughly mixed, and ground by an ultrafine grinder to obtain 30% compound 2 powder.

Example 35: Preparation of 50% Compound 2 Soluble Powder

According to the formula requirements, 50 parts of compound 2, 3 parts of sodium dodecyl sulfate, 4 parts of sodium salt of alkyl naphthalene sulfonic acid polycondensate, 4 parts of EFW 5 parts of hydroxypropyl cellulose and ammonium sulfate to make up to 100% were thoroughly mixed, and ground by an ultrafine grinder to obtain 50% compound 2 soluble powder.

Example 36: Preparation of 10% Compound 2 Tablets

According to the formula requirements, 10 parts of compound 2, 2 parts of sodium methyl naphthalene sulfonate-formaldehyde condensate, 1 part of sodium dodecyl sulfate, 15 parts of soluble starch, 8 parts of sodium sulfate, 5 parts of white carbon black and diatomite to make up to 100% were thoroughly mixed, ground by an ultrafine grinder and then tabletted to obtain 10% compound 2 tablets.

Determination of Biological Activity

Example 37: Determination of Acaricidal Activity

The acaricidal activity in a greenhouse was determined by using the compound of the present invention. The determination method is as follows:

According to the solubility of the compound to be tested, the compound was dissolved with acetone or dimethyl sulfoxide, and prepared into 50 ml of solution to be tested in a concentration needed with 0.1% Tween 80 solution, in which the content of acetone or dimethyl sulfoxide comprises not more than 0%/o.

37.1 Determination of Adult Activity of *Tetranychus cinnabarinus*

A marrow bean seedling with two true leaves was taken and inoculated with adult mites of *Tetranychus cinnabarinus*, and after examination of the base number, the whole plant was sprayed with a hand-held sprayer. Every treatment was performed for three times, After the treatment, the seedling was placed in a standard observation room, and the number of surviving mites was examined after 72 hours to calculate the mortality rate.

Test results are as follows:

When the concentration of the chemical solution was 5 mg/L, compounds 1, 2, 97, 98 and intermediate compounds II.1. II.2. II.63. II.64 have a lethal rate of not less than 90% for *Tetranychus cinnabarinus*.

37.2 Determination of Activity of *Tetranychus cinnabarinus* Eggs

A potted marrow bean seedling with two true leaves was taken, one true leaf was removed, then 10 female adult mites of healthy *Tetranychus cinnabarinus* were inoculated to the leaf, the adult mites were removed after 24 hours, spray treatment was performed after examination of the number of eggs. Every treatment was performed for 3 times. After 5 days, when all the blank control eggs were incubated, the number of the eggs which were not incubated in each treatment was examined to calculate the incubation inhibition rate.

Test results are as follows:

When the concentration of the chemical solution was 5 mg/L, compounds 1, 2, 97, 98 and intermediate compounds II.1, II.2, II.63, II.64 have a hatching inhibition rate of not less than 90% for *Tetranychus cinnabarinus* eggs.

The invention claimed is:

1. A trifluoroethyl thioether (sulfoxide) substituted benzene compound, wherein, the compound is as shown in formula I:

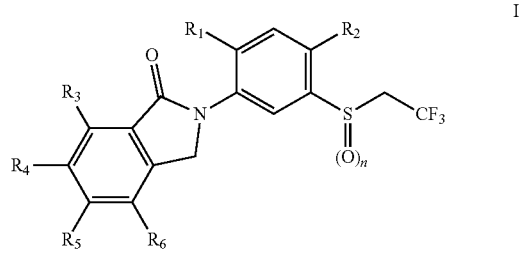

where:
$R_1$, $R_2$ are independently selected from hydrogen, halogen, cyano, $C_1$-$C_4$ alkyl or $C_1$-$C_4$ haloalkyl;
n is selected from 0 or 1;
$R_3$, $R_4$, $R_5$ and $R_6$ are independently selected from hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy.

2. The compound of claim 1, wherein, in the formula I:
$R_1$, $R_2$ are independently selected from hydrogen, fluorine, chlorine, bromine, cyano or methyl;
n is selected from 0 or 1;
$R_3$, $R_4$, $R_5$ and $R_6$ are independently selected from hydrogen, fluorine, chlorine, bromine, cyano, nitro, methyl, ethyl, n-propyl, isopropyl, n-butyl, isobutyl, tert-butyl, trifluoromethyl, methoxy, ethoxy or trifluoromethoxy.

3. The compound of claim 2, wherein, in the formula I:
$R_1$ is selected from fluorine;
$R_2$ is selected from methyl;
n is selected from 0 or 1;
$R_3$, $R_4$ and $R_6$ are selected from hydrogen; and
$R_5$ is selected from hydrogen or cyano.

4. An intermediate compound for preparing the trifluoroethyl thioether (sulfoxide) substituted benzene compound of claim 1, wherein the intermediate compound is as shown in formula II:

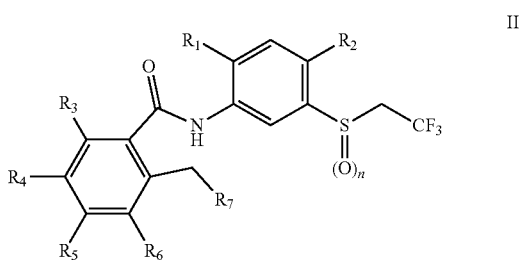

where:
- $R_1$, $R_2$ are independently selected from hydrogen, halogen, cyano, $C_1$-$C_4$ alkyl or $C_1$-$C_4$ haloalkyl;
- n is selected from 0 or 1;
- $R_3$, $R_4$, $R_5$ and $R_6$ are independently selected from hydrogen, halogen, cyano, nitro, $C_1$-$C_4$ alkyl, $C_1$-$C_4$ haloalkyl, $C_1$-$C_4$ alkoxy or $C_1$-$C_4$ haloalkoxy; and
- $R_7$ is selected from chlorine or bromine.

5. A method of preparing acaricides in fields of agriculture, forestry and health using a compound of formula I of claim 1.

6. An acaricidal composition, wherein: the composition comprises the compound of formula I of claim 1 as an active component, and the active component is 0.1-99% by the weight of the composition.

7. A method for controlling agricultural or forestry pest mites, wherein: an effective amount of the composition of claim 6 is administrated to the pest mites to be controlled or growth medium thereof.

* * * * *